United States Patent [19]

Watson

[11] 3,934,001

[45] Jan. 20, 1976

[54] ORAL COMPOSITIONS CONTAINING GERMICIDALLY ACTIVE PLASTIC POWDERS

[75] Inventor: Charles Andrew Watson, Ruislip, England

[73] Assignee: Lever Brothers Company, New York, N.Y.

[22] Filed: July 31, 1970

[21] Appl. No.: 64,126

Related U.S. Application Data

[63] Continuation of Ser. No. 836,217, June 12, 1969, abandoned, which is a continuation of Ser. No. 599,692, Dec. 7, 1966, abandoned.

[30] Foreign Application Priority Data

Dec. 7, 1965 United Kingdom............... 51752/65

[52] U.S. Cl. ..................... 424/49; 424/78; 424/81; 424/83
[51] Int. Cl.² ........................................... A61A 7/16
[58] Field of Search ................................ 424/49–58

[56] References Cited
FOREIGN PATENTS OR APPLICATIONS
1,504,155 10/1967 France................................ 424/49

OTHER PUBLICATIONS

Accepted Dental Therapeutics, 1969/1970, 33rd edition, published by the American Dental Association, Chicago, pp. 140 and 148.
Dubos et al, Bacterial and Mycotic Infections of Man, 2nd ed., published by J. B. Lippincott Co., Phila., 1952, p. 663.
Simonds-Church, The Encyclopedia of Basic Materials for Plastics, published by Reinhold Publishing Co., 1967, p. 246.
Accepted Dental Therepeutics, 1969/1970, 33rd edition, published by the American Dental Association, Chicago, p. 245.
The Washington Sunday Star, July 27, 1969, p. B-2.

Primary Examiner—Richard L. Huff
Attorney, Agent, or Firm—Arnold Grant, Esq.

[57] ABSTRACT

Oral compositions are disclosed which contain germicidally active plastic powders. The plastic powders employed are resinous materials having a germicide absorbed therein preferably in a concentration of at least about 0.1% by weight of the resin. Germicides and plastic powders suitable for use in oral compositions are discussed.

6 Claims, No Drawings

ORAL COMPOSITIONS CONTAINING GERMICIDALLY ACTIVE PLASTIC POWDERS

This application is a continuation of Ser. No. 836,217, filed June 12, 1969, which in turn is a continuation of Ser. No. 599,692, filed Dec. 7, 1966, both now abandoned.

This invention relates to oral compositions.

It has been proposed to include germicides, for example hexachlorophene, in compositions for oral hygiene. Examples of such compositions where inclusion of a germicide has been proposed are dentifrices and mouthwashes. The inclusion of germicides in such compositions produces a beneficial effect in the mouth but it is however limited because the germicide is retained in the oral cavity for only a short time.

It is an object of the present invention to provide a means of producing a longer germicidal effect in the mouth.

It has been found that this can be achieved by including in the oral composition, particles of a water-insoluble material which have been pretreated with a germicide so that they are impregnated with the germicide. The longer-lasting germicidal effect produced by oral compositions incorporating such germicide-containing particles is believed to be due to the trapping of some of the particles in crevices in the mouth and release of germicide from such particles.

Accordingly, the present invention provides an oral composition comprising particles of a water-insoluble material which have been impregnated with a germicide.

The water-insoluble material should, of course, be non-toxic, the particles are preferably white or nearly white. Suitable as the particles are plastic materials, especially thermoplastic resins. Preferred plastics materials are polyvinylchloride, polyethylene, polypropylene, polymethylmethacrylate, and copolymers of polyvinylchloride and polyvinylalcohol. The particles desirably have a size less than 50 microns. Especially suitable are particles having a size within the range 0.1 to 20 microns. While hexachlorophene is the preferred germicide that is used, other germicides known in the art as suitable for use in oral hygiene may be used, for example chlorhexidene, tyrothricin and quaternary ammonium germicides.

The particles of the water-insoluble material may be impregnated with the germicide by pretreating them with a solution of the germicide in a solvent capable of being absorbed by the particles whereby the germicide diffuses into and is absorbed by the particles. To increase the rate of diffusion of the solvent and germicide into the particles the treatment is preferably carried out at an elevated temperature.

The oral composition may be in the form of a dentifrice or in the form of a mouthwash or other product for the care of the oral cavity. If the oral composition is a dentifrice this may be in the form of a liquid, paste, powder, tablets or solid block. The amount of the germicide containing particles in the oral preparation will be chosen to suit the particular form of the product. In a toothpaste dentifrice for example, suitable amounts of the germicide-containing particles are from 1 to 50% by weight, preferably 3 to 35% by weight. The amount used in the dentifrice or other oral composition will also be chosen having regard to the amount of the germicide in the particles.

The amount of the germicide in the particles is preferably at least 0.05% by weight of the oral composition.

The oral composition will also comprise the usual ingredients. Thus, toothpastes, for instance, will usually comprise abrasive material, humectant, binder, foaming agent, sweetening agent and flavouring agent, and may also contain germicide other than that in the particles.

It is believed that the germicide-containing water-insoluble particles employed in the above oral compositions are themselves novel, and in accordance with another aspect of the present invention, the invention also relates to such germicide-containing particles themselves. The particles preferably contain at least 0.1% by weight of absorbed germicide, preferably 1% or more of germicide.

The invention also relates to a method of making an oral composition comprising the steps of contacting particles of a water-insoluble material with a germicide in solution in a solvent capable of being absorbed by the particles, separating, if desired, the particles containing absorbed solvent and germicide from any excess solvent and germicide, and including the germicide-containing particles in an oral composition.

The following Examples illustrate the invention. Parts are by weight.

EXAMPLE 1

1 part of hexachlorophene was dissolved in a mixture of 5 parts of propylene glycol and 20 parts of glycerine. 10 parts of polyvinylchloride powder (particle size in the range 1 to 20 microns) were then added. The mixture was stirred at 90° to 100°C. for 1 to 2 hours. The mixture was then cooled and the powdered plastics material filtered off, washed with hot propylene glycol followed by distilled water and dried in an oven at 50°C. The content of hexachlorophene in the particle was determined and found to be 6% by weight. The particles were then included in a dentifrice.

A typical composition of a dentifrice containing the polyvinylchloride particles is the following:

| Ingredient | Parts |
| --- | --- |
| Plastics material impregnated with germicide | 30.0 |
| Polishing Agent | 12.5 |
| Humectant | 18.0 |
| Binding Agent | 1.6 |
| Foaming Agent | 1.5 |
| Sweetening Agent | 0.2 |
| Flavouring Agent | 1.0 |
| Water | to 100.0 |

EXAMPLE 2

5 parts of hexachlorophene were dissolved in a mixture of 20 parts cineole and 18 parts propylene glycol. 50 parts of polyethylene powder (particle size in the range 1 to 20 microns) were added and the mixture heated at 70°C. for three hours with stirring. The powdered polyethylene was then filtered off, washed with hot propylene glycol followed by distilled water and dried in an oven at 50°C. The amount of hexachlorophene introduced in the polyethylene particles was 1.25% by weight.

A typical composition of a dentifrice comprising the germicide-containing polyethylene powder produced as above is the following:

| Ingredient | Parts |
|---|---|
| Polyethylene powder impregnated with germicide | 25.0 |
| Polishing Agent | 12.5 |
| Humectant | 20.0 |
| Foaming Agent | 1.2 |
| Binding Agent | 1.4 |
| Sweetening Agent | 0.2 |
| Flavouring Agent | 1.0 |
| Water | to 100.0 |

Toothpastes having the compositions indicated in Examples 1 and 2 were stored at 37°C. for times as indicated in the Table below. The plastics materials were then separated from the toothpastes and the level of hexachlorophene in them determined. The results are indicated in the Table.

TABLE

| | Content of Hexachlorophene (after time indicated) | | | | | |
|---|---|---|---|---|---|---|
| | Initially | 1 day | 3 days | 7 days | 17 days | 63 days |
| Ex. 1 | 6.0 | 5.6 | 5.3 | — | 4.6 | 4.6 |
| Ex. 2 | 1.25 | 0.88 | 0.34 | 0.32 | — | — |

The results show that an equilibrium is reached between the germicide in the polymer and the germicide in the aqueous toothpaste phase.

EXAMPLE 3

2.5 parts of hexachlorophene were dissolved in 100 parts of propylene glycol. 25 parts of polymethylmethacrylate powder (particle size in the range 1 to 20 microns) were added and the mixture heated at 90°C. for three hours. The polymethylmethacrylate particles were then filtered off, washed with hot propylene glycol followed by distilled water and dried in an oven at 50°C. The amount of hexachlorophene introduced in the plastics particles was 0.25% by weight.

The plastics particles containing hexachlorophene may be included in a toothpaste of the composition described in Example 1 or Example 2.

EXAMPLE 4

1 part of hexachlorophene was dissolved in a mixture of 12.5 parts of propylene glycol and 12.5 parts of glycerine. 10 parts of a powdered copolymer of polyvinylchloride and (10%) polyvinyl alcohol (particle size in the range 1 to 20 microns) were added. The mixture was stirred at 90°C. for three hours. the powdered plastics material was then filtered off, washed with hot propylene glycol followed by distilled water and dried at 50°C. The amount of hexachlorophene contained in the polymer was about 2.4% by weight.

The plastics particles containing hexachlorophene may be included in a toothpaste of the composition described in Example 1 or Example 2.

EXAMPLE 5

The following is an example of typical mouthwash preparation in accordance with the invention.

| Ingredient | Parts |
|---|---|
| Polyvinylchloride impregnated with germicide, prepared as described in Example 1 | 5.00 |
| Ethyl alcohol | 20.00 |
| Flavour | 0.08 |
| Polyoxyethylene stearyl ether | 0.12 |
| Saccharin | 0.02 |
| Water | to 100.00 |

I claim:

1. In a liquid mouthwash preparation having a liquid vehicle and an effective amount of a germicide suitable for use in oral hygiene, the improvement which comprises providing said germicide in the form of non-toxic, water-insoluble thermoplastic resinous particles having a size less than 50 microns, said particles being impregnated with said germicide suitable for use in oral hygiene in an amount of at least about 0.1 per cent of said particles by weight.

2. A mouthwash preparation in accordance with claim 1 wherein said water-insoluble thermoplastic resinous particles are between 0.1 and 20 microns in diameter.

3. A mouthwash preparation in accordance with claim 1 wherein the amount of said water-insoluble thermoplastic resinous germicide-impregnated particles is sufficient to provide at least 0.05 per cent germicide by weight of the mouthwash composition.

4. A mouthwash preparation in accordance with claim 1 wherein said water-insoluble thermoplastic resinous particles are selected from the group consisting of polyvinylchloride, polyethylene, polypropylene, polymethylmethacrylate and copolymers of polyvinylchloride and polyvinyl alcohol.

5. A mouthwash preparation in accordance with claim 1 wherein said germicide is hexachlorophene.

6. A mouthwash preparation in accordance with claim 1 wherein said water-insoluble thermoplastic resinous germicide impregnated particles contain at least about 1 per cent by weight germicide.

* * * * *